(12) United States Patent
Gengrinovitch et al.

(10) Patent No.: US 11,058,701 B2
(45) Date of Patent: *Jul. 13, 2021

(54) CYTARABINE CONJUGATES FOR CANCER THERAPY

(71) Applicant: BIOSIGHT LTD., Lod (IL)

(72) Inventors: Stela Gengrinovitch, Kfar Hanania (IL); Ruth Ben Yakar, Shoham (IL)

(73) Assignee: Biosight Ltd., Lod (IL)

(*) Notice: Subject to any disclaimer, the term of this patent is extended or adjusted under 35 U.S.C. 154(b) by 0 days.

This patent is subject to a terminal disclaimer.

(21) Appl. No.: 15/780,732

(22) PCT Filed: Jan. 25, 2016

(86) PCT No.: PCT/IL2016/050077
§ 371 (c)(1),
(2) Date: Jun. 1, 2018

(87) PCT Pub. No.: WO2017/093993
PCT Pub. Date: Jun. 8, 2017

(65) Prior Publication Data
US 2018/0369265 A1     Dec. 27, 2018

Related U.S. Application Data

(60) Provisional application No. 62/262,428, filed on Dec. 3, 2015.

(51) Int. Cl.
| *A01N 43/04* | (2006.01) |
| *A61K 31/70* | (2006.01) |
| *A61K 31/7068* | (2006.01) |
| *A61K 47/54* | (2017.01) |
| *A61P 35/00* | (2006.01) |

(52) U.S. Cl.
CPC ........ *A61K 31/7068* (2013.01); *A61K 47/542* (2017.08); *A61P 35/00* (2018.01)

(58) Field of Classification Search
None
See application file for complete search history.

(56) References Cited

U.S. PATENT DOCUMENTS

| 2,949,451 | A | 8/1960 | Hoffer |
| 3,041,335 | A | 6/1962 | Hoffer |
| 4,179,337 | A | 12/1979 | Davis et al. |
| 4,296,105 | A | 10/1981 | Baurain et al. |
| 4,348,522 | A | 9/1982 | Schultz et al. |
| 5,106,951 | A | 4/1992 | Morgan et al. |
| 5,643,957 | A | 7/1997 | Leone-Bay et al. |
| 5,650,386 | A | 7/1997 | Leone-Bay et al. |
| 5,962,216 | A | 10/1999 | Trouet et al. |
| 6,344,213 | B1 | 2/2002 | Leone-Bay et al. |
| 6,428,780 | B2 | 8/2002 | Leone-Bay et al. |
| 6,617,306 | B2 | 9/2003 | Stein et al. |
| 6,623,731 | B2 | 9/2003 | Leone-Bay et al. |
| 7,151,092 | B2 | 12/2006 | Boyer et al. |
| 7,989,188 | B2 | 8/2011 | Gengrinovitch et al. |
| 8,993,278 | B2 | 3/2015 | Gengrinovitch et al. |
| 2011/0275590 | A1* | 11/2011 | Gengrinovitch ............ A61K 47/48038 514/49 |
| 2014/0227282 | A1 | 8/2014 | Nishitani et al. |

FOREIGN PATENT DOCUMENTS

| CN | 101812105 A | 8/2010 |
| JP | H0859688 A | 3/1996 |
| RU | 2085557 C1 | 7/1997 |
| WO | 95/18636 A2 | 7/1995 |
| WO | WO/1996/030036 A1 | 10/1996 |
| WO | WO/1997/036480 A1 | 10/1997 |
| WO | 00/33888 A2 | 6/2000 |
| WO | 2005/072061 A2 | 8/2005 |
| WO | WO/2008/072963 A1 | 6/2008 |
| WO | WO/2014/097318 A2 | 3/2015 |
| WO | WO/2015/178265 A1 | 11/2015 |

OTHER PUBLICATIONS

Chhikara et al. Expert Opin. Drug Deliv. (2010), vol. 7, pp. 1399-1414.*
Fasinu et al. Biopharmaceuticals & Drug Disposition (2011), vol. 32, pp. 185-209.*
Becker et al. British Journal of Haematology (2011), vol. 155, pp. 182-189.*
Brynes et al., (1978) Potential antitumor agents via inhibitors of L-asparagine synthetase: Substituted sulfonamides and sulfonyl hydrazides related to glutamine. Journal of pharmaceutical sciences, 67(11), 1550-1553.
Brynes et al., (1978) Potential inhibitors of L-asparagine biosynthesis. 4. Substituted sulfonamide and sulfonylhydrazide analogs of L-asparagine. Journal of medicinal chemistry, 21(1), 45-49.
Cheon et al., (2006) Enhanced cellular uptake of Ara-C via a peptidomimetic prodrug, L-valyl-ara-C in Caco-2 cells. Journal of pharmacy and pharmacology, 58(7), 927-932.
Chhikara et al., (2010) Development of cytarabine prodrugs and delivery systems for leukemia treatment. Expert opinion on drug delivery, 7(12), 44 pages.
Heinemann et al., (1988) Comparison of the cellular pharmacokinetics and toxicity of 2', 2'-difluorodeoxycytidine and 1-β-d-arabinofuranosylcytosine. Cancer research, 48(14), 4024-4031.
Hertel et al., (1990) Evaluation of the antitumor activity of gemcitabine (2', 2'-difluoro-2'-deoxycytidine). Cancer research, 50(14), 4417-4422.
Ho, (1974) Biochemical studies of a new antitumor agent, O2, 2'-cyclocytidine. Biochemical pharmacology, 23(8), 1235-1244.
Kato et al., (1984) Antitumor activity of 1-β-d-arabinofuranosylcytosine conjugated with polyglutamic acid and its derivative. Cancer research, 44(1), 25-30.

(Continued)

*Primary Examiner* — Patrick T Lewis
(74) *Attorney, Agent, or Firm* — Mark S. Cohen; Pearl Cohen; Zedek Latzer Baratz LLP

(57) ABSTRACT

Provided relates to conjugates including cytarabine and an amino acid for use in the treatment of cancer. Further, the subject matter relates to conjugates of cytarabine and aspartic acid for use in the treatment of hematological cancers in medically compromised patients.

14 Claims, 4 Drawing Sheets

(56) References Cited

OTHER PUBLICATIONS

Kodama et al., (1989) Antitumor Activity and Pharmacology of 1-β-D-Arabinofuranosylcytosine-5'-stearylphosphate: An Orally Active Derivative of 1-β-D-Arabinofuranosylcytosine. Cancer Science, 80(7), 679-685.
Manfredini et al., (2000) Peptide T-araC conjugates: solid-phase synthesis and biological activity of N4-(acylpeptidyl)-araC. Bioorganic & medicinal chemistry, 8(3), 539-547.
Novotny et al., (2008) Cytarabine conjugates with biologically active molecules and their potential anticancer activity. Neoplasma, 56(3), 177-186.
Renis, (1973) Antiviral Activity of Cytarabine in Herpesvirus-Infected Rats. Antimicrobial agents and chemotherapy, 4(4), 439-444.
Stammer et al., (1978) 5-Carboxamido-4-amino-3-isoxazolidone, an asparagine analog. Journal of medicinal chemistry, 21(7), 709-712.
Woodcock et al., (1980) Biochemical, pharmacological, and phase I clinical evaluation of pseudoisocytidine. Cancer research, 40(11), 4243-4249.
Zuckerman et al., (2015) Astarabine, a Pro-Drug of Cytarabine, Is Safe for Patients with Advanced Acute Leukemia. A Phase I/IIa Single Center Study in Relapsed/Refractory or Medically Unfit Patients. 3 Pages.
Beran, M., Shen, Y., Kantarjian, H., O'Brien, S., Koller, C. A., Giles, F. J., . . . & Estey, E. H. (2001). High-dose chemotherapy in high-risk myelodysplastic syndrome: Covariate-adjusted comparison of five regimens. Cancer, 92(8), 1999-2015.
Dalal, M., Plowman, J., Breitman, T. R., Schuller, H. M., del Campo, A. A., Vistica, D. T., . . . & Johns, D. G. (1986). Arabinofuranosyl-5-azacytosine: antitumor and cytotoxic properties. Cancer research, 46(2), 831-838.
Definition of Derivative by Merriam-Webster Online Dictionary, https://www.merriam-webster.com/dictionary/derivative (Sep. 18, 2019).
Döhner, H., Lübbert, M., Fiedler, W., Fouillard, L., Haaland, A., Brandwein, J. M., . . . & Müller-Tidow, C. (2014). Randomized, phase 2 trial of low-dose cytarabine with or without volasertib in AML patients not suitable for induction therapy. Blood, 124(9), 1426-1433.
Extended European Search Report for corresponding European Patent Application No. EP16870114.2 dated Jun. 17, 2019.
Extended European Search Report for corresponding European Patent Application No. EP16870129.0 dated Jun. 21, 2019.
Fasinu, P., Pillay, V., Ndesendo, V. M., du Toit, L. C., & Choonara, Y. E. (2011). Diverse approaches for the enhancement of oral drug bioavailability. Biopharmaceutics & drug disposition, 32(4), 185-209.
Fong, W. F., & Law, C. L. (1988). Possible role of the membrane Na+/H+ antiport in ornithine decarboxylase induction by L-asparagine. Biochemical and biophysical research communications, 155(2), 937-942.
Gengrinovitch, S., Yakar, R. B., Zuckerman, T., Krivoy, N., & Rowe, J. M. (Dec. 3, 2015), "Astarabine, a Cytarabine Pro-Drug, Is Safe and Efficacious in the Treatment of Leukemia—Results of Animal Studies". Blood, vol. 126, No. 23, pp. 2545. 57th Annual Meeting of the American Society of Hematology, ASH 2015, San Diego, CA, United States.
Hasabelnaby, S., Goudah, A., Agarwal, H. K., & Tjarks, W. (2012). Synthesis, chemical and enzymatic hydrolysis, and aqueous solubility of amino acid ester prodrugs of 3-carboranyl thymidine analogs for boron neutron capture therapy of brain tumors. European journal of medicinal chemistry, 55, 325-334.
International Search Report for PCT Application No. PCT/IL2016/050077 dated May 16, 2016.
International Search Report for PCT Application No. PCT/IL2016/051287 dated Mar. 26, 2017.

Jin, M. J., Hong, J. H., & Han, H. K. (2008). Synthesis and In-vitro Evaluation of N4-Amino Acid Derivatives of Cytarabine for Improving the Oral Delivery of Cytarabine. Journal of Pharmaceutical Investigation, 38(4), 255-259.
Liu, B., Cui, C., Duan, W., Zhao, M., Peng, S., Wang, L., . . . & Cui, G. (2009). Synthesis and evaluation of anti-tumor activities of N4 fatty acyl amino acid derivatives of 1-β-arabinofuranosylcytosine. European journal of medicinal chemistry, 44(9), 3596-3600.
Löwenberg, B., Pabst, T., Vellenga, E., van Putten, W., Schouten, H. C., Graux, C., . . . & de Greet, G. E. (2011). Cytarabine dose for acute myeloid leukemia. New England Journal of Medicine, 364(11), 1027-1036.
Patel, P. L. (2014). Targeting GRP78 in Cancer with Nucleic Acid Bioconjugates. Ph D. Thesis. Seton Hall University South Drange, NJ, USA, 155 pages.
Piek, J., Adelt, T., Huse, K., & Bock, W. J. (1987). Cerebrospinal fluid and plasma aminograms in patients with primary and secondary tumors of the CNS. Infusionstherapie und klinische Ernährung, 14(2), 73-77. Abstract in English.
Singh, V. K., & Subudhi, B. B. (2015). Development of reversible glutamine conjugate of methotrexate for enhanced brain delivery. Medicinal Chemistry Research, 24(2), 624-635.
Warrell Jr, R. P., & Berman, E. (1986). Phase I and II study of fludarabine phosphate in leukemia: therapeutic efficacy with delayed central nervous system toxicity. Journal of Clinical Oncology, 4(1), 74-79.
Zuckerman T. (Sep. 9, 2015). Study Evaluating the Safety and Efficacy of Astarabine in Acute Myeloid Leukemia or Acute Lymphoblastic Leukemia (BSTPHASE1-01), BioSight Ltd., ClinicalTrials.gov Identifier: NCT02544438, retrieved on-line at: https://clinicaltrials.gov/ct2/show/NCT02544438.
Anonymous, "Study Evaluating the Safety and Efficacy of Astarabine in Acute Myeloid Leukemia or Acute Lymphoblastic Leukemnia (BSTPHASE1-01)", Clinical Trials.gov, Sep. 9, 2015 (Sep. 9, 2015), pp. 1-7, retrieved Jun. 3, 2019, https://clinicaltrials.gov/ct2/show/record/NCT02544438?view=record.
Burk, M., Heyll, A., Arning, M., Volmer, M., Fartash, K., & Schneider, W. (1997). Pharmacokinetics of high-dose cytarabine and its deamination product—a reappraisal. Leukemia & lymphoma, 27(3-4), 321-327.
Capizzi, R. L., Yang, J. L., Cheng, E., Bjornsson, T., Sahasrabudhe, D., Tan, R. S., & Cheng, Y. C. (1983). Alteration of the pharmacokinetics of high-dose ara-C by its metabolite, high ara-U in patients with acute leukemia. Journal of Clinical Oncology, 1(12), 763-771.
DeAngelis, L. M., Kreis, W., Chan, K., Dantis, E., & Akerman, S. (1992). Pharmacokinetics of ara-C and ara-U in plasma and CSF after high-dose administration of cytosine arabinoside. Cancer chemotherapy and pharmacology, 29(3), 173-177.
Reese, N. D., & Schiller, G. J. (2013). High-dose cytarabine (HD araC) in the treatment of leukemias: a review. Current hematologic malignancy reports, 8(2), 141-148.
Zuckerman, T., Ram, R., Akria, L., Koren-Michowitz, M., Hoffman, R., Henig, I., . . . & Tavor, S. (2019). BST-236, a novel cytarabine prodrug for patients with acute leukemia unfit for standard induction: a phase 1/2a study. Blood advances, 3(22), 3740-3749.
Altman J. K. et al (2019). Aspacytarabine (BST-236) Is Safe and Efficacious As a Single-Agent, First-Line Therapy for Patients with Acute Myeloid Leukemia Unfit for Standard Chemotherapy. The 61st Annual ASH Meeting in Orlando.
Day, C. P., Merlino, G., & Van Dyke, T. (2015). Preclinical mouse cancer models: a maze of opportunities and challenges. Cell, 163(1), 39-53.
Singh, M., & Ferrara, N. (2012). Modeling and predicting clinical efficacy for drugs targeting the tumor milieu. Nature biotechnology, 30(7), 648-657.
Wall, R. J., & Shani, M. (2008). Are animal models as good as we think?. Theriogenology, 69(1), 2-9.
Bishop, J. F. et al. (1996). A randomized study of high-dose cytarabine in induction in acute myeloid leukemia.
Ferreri, A. J. et al. (2009). High-dose cytarabine plus high-dose methotrexate versus high-dose methotrexate alone in patients with primary CNS lymphoma: a randomised phase 2 trial. The Lancet, 374(9700), 1512-1520.

(56) References Cited

OTHER PUBLICATIONS

Tilborg, A. et al. (2014). Pharmaceutical salts and cocrystals involving amino acids: a brief structural overview of the state-of-art. European journal of medicinal chemistry, 74, 411-426.

* cited by examiner

CYTARABINE CONJUGATES FOR CANCER THERAPY

CROSS REFERENCE TO RELATED APPLICATIONS

This application is a National Phase Application of PCT International Application No. PCT/IL2016/050077, International Filing Date Jan. 25, 2016, claiming the benefit of U.S. Patent Application No. 62/262,428, filed Dec. 3, 2015, which are hereby incorporated by reference.

FIELD OF THE INVENTION

The present invention relates to conjugates comprising cytarabine and an amino acid for use in the treatment of cancer. In particular, the present invention relates to conjugates of cytarabine and aspartic acid for use in the treatment of hematological cancers in medically compromised patients.

BACKGROUND OF THE INVENTION

Anti-Proliferative Drugs

Anti-proliferative drugs, also known as anti-metabolites, anti-neoplastic agents or covalent DNA binding drugs, act by inhibiting essential metabolic pathways and are commonly used in the treatment of malignant diseases. However, their high toxicity to normal cells and severe side effects limit their use as therapeutic agents. Undesirable side effects include anemia, emesis and balding due to cytotoxic effects on rapidly dividing normal cells, such as stem cells in the bone marrow, epithelial cells of the intestinal tract, hair follicle cells, etc.

Another major problem associated with anti-proliferative drugs is inherent or acquired resistance of tumors to the drugs. For example, although the initial remission rate following treatment with L-asparaginase is quite high in acute lymphoblastic leukemia (ALL) patients, relapse and associated drug resistance pose a significant clinical problem. Studies have demonstrated increased asparagine synthetase (AS) expression in asparaginase-resistant cells, which has led to the hypothesis that elevated AS activity permits drug-resistant survival of malignant cells.

Nucleotide/Nucleoside Analogs

Nucleoside analogs compete with their physiologic counterparts for incorporation into nucleic acids and have earned an important place in the treatment of acute leukemia. The most important of these are the arabinose nucleosides; a unique class of antimetabolites originally isolated from the sponge *Cryptothethya crypta*, but now produced synthetically. They differ from the physiologic deoxyribonucleosides by the presence of a 2'-OH group in the cis configuration relative to the N-glycosyl bond between cytosine and arabinoside sugar. Several arabinose nucleosides have useful antitumor and antiviral effects. The most active cytotoxic agent of this class is cytosine arabinoside (cytarabine or ara-C). Cytarabine is currently used for treating cancers of white blood cells such as Acute Myeloid Leukemia (AML), Acute Lymphoblastic Leukemia (ALL), Chronic Myeloid Leukemia (CML), Chronic Lymphoblastic Leukemia (CLL), and Myelodysplastic Syndromes (MDS). However, cytarabine is highly toxic having severe side-effects such as cerebellar toxicity and bone marrow suppression. Cytarabine treatment is therefore limited, and often restricted, in elderly patients and in patients having hepatic, renal, or cerebellar dysfunction.

One objective of analog development in the area of cytidine antimetabolites has been to find compounds that preserve the inhibitory activity of ara-C but are resistant to deamination. A number of deaminase-resistant analogs have been developed, including cyclo-cytidine (Ho D H W, 1974) and $N^4$-behenoyl ara-C (Kodama et al., 1989) that showed anti-leukemic activity in some clinical trials, but had undesirable side effects (Woodcock et al., 1980). Other representative compounds are $N^4$-Palmitoyl-ara-C, 2'-Azido-2'-deoxy ara-C, 5'-(Cortisone 21-phosphoryl) ester of ara-C, 5'-Acyl esters of ara-C (e.g., 5'-palmitate ester), $N^4$ Behenoyl-ara-C, ara-C conjugate with poly-$H^5$ (2-hydroxyethyl)-L-glutamine, Dihydro-5-azacytidine, 5-Aza-arabinosylcytosine, 5-Aza 2'-deoxycytidine and 2'-2'-Difluorodeoxycytidine (Hartel et al., 1990 and Heineman et al., 1988).

Gemcitabine (2,2-difluorodeoxycytidine, dFdC) is the most important cytidine analog to enter clinical trials since ara-C. It has become incorporated into the standard first-line therapy for patients with pancreatic cancer, lung cancer, and transitional cell cancer of the bladder.

Nucleotide analogs have also been used in non-cancer applications. For example Flucytosine, a fluorinated cytosine analog, is used as an antifungal agent.

Amino Acids and Proliferative Disease

Asparagine is a non-essential amino acid that is required by rapidly proliferating cells. Mammalian cells can synthesize asparagine from aspartate using the ATP-dependent enzyme asparagine synthetase (EC 6.3.5.4), which transfers the amino group from the amide of glutamine to the β-carboxyl of aspartate in a reaction that can be represented as: Glutamine+Aspartate+ATP+$H_2O$=Glutamate+Asparagine+AMP+PPi.

Malignant cells often require higher amounts of amino acids, including asparagine, to support their metabolism and proliferation. In order to fulfill the need for high amounts of amino acids, malignant cells develop the ability to actively transport amino acids from their environment. Moreover, asparagine synthetase deficiency occurs in certain tumors, causing them to rely on an external supply of asparagine from other sources, such as serum. This observation led to the development of the enzyme L-asparaginase (CE 3.5.1.1) as a chemotherapeutic agent. L-asparaginase hydrolyzes L-asparagine to aspartate and ammonia, hence depleting L-asparagine from the serum and inhibiting tumor growth. L-asparaginase is used mainly in the treatment of Acute Lymphoblastic Leukemia (ALL) and shows some activity against other hematological cancers including acute non-lymphocytic leukemia.

The L-asparaginase used in the clinic is available in two unmodified (native) forms purified from bacterial sources, and one as a PEGylated compound. U.S. Pat. No. 4,179,337 teaches PEGylated L-asparaginase, wherein the enzyme is coupled to PEG having a molecular weight of about 500 to 20,000 Daltons.

The in vivo down-regulation of asparagine synthetase may provide an efficient mechanism for inhibiting tumor growth. However, cells respond to amino acid deprivation by a concerted increase in asparagine synthetase mRNA, protein, and enzymatic activity that involves transcriptional control of the asparagine synthetase gene.

A metabolic approach was initially used to inhibit the activity of asparagine synthetase by the generation of L-asparagine and L-aspartic acid analogs. Analogs including 5-carboxamido-4-amino-3-isoxazolidone (Stammer et al., 1978) and N-substituted sulfonamides and N'-substituted sulfonylhydrazides have been prepared as sulfur analogues of L-asparagine (Brynes S et al., 1978a; Brynes S et al., 1978b). U.S. Pat. No. 4,348,522 teaches the salt of PALA, N-phosphonacetyl-L-aspartic acid, which has been shown to exhibit anti-tumor activity and is presently in clinical trials as combination chemotherapy for colorectal and pancreatic cancers.

Aspartic acid-ara-C was used as a raw material for the synthesis of peptide T-ara-C conjugates for targeting CD4 positive cells (Manfredini et al., 2000).

The use of prodrugs to impart desired characteristics such as increased bioavailability or increased site-specificity is a recognized concept in the art of pharmaceutical development. For example, direct or indirect conjugation of a drug to an antibody creates a stable conjugate that can arrive at the target site with minimum dissociation of the drug. Drug targeting may be combined with a mechanism of selective release of the drug for maximal potency.

U.S. Pat. No. 4,296,105 describes doxorubicin derivatives linked to an optionally substituted amino acid at the hydroxy group of the amino acid residue, which possess in vitro a higher antitumor activity and lower toxicity than doxorubicin.

U.S. Pat. No. 5,962,216 teaches tumor activated prodrugs which are unable to enter the cell until cleaved by a factor or factors secreted by a target cell.

U.S. Pat. No. 5,650,386 teaches compositions comprising at least one active agent, and at least one modified non-alpha amino acid or poly amino acid, which acts as a carrier of the active agent. The amino acid modification includes acylation or sulfonation of at least one free amine group.

U.S. Pat. Nos. 6,623,731; 6,428,780 and 6,344,213 teach non-covalent mixtures comprising modified amino acids as carriers for biologically active agents.

U.S. Pat. No. 5,106,951 discloses a conjugate comprising an aromatic drug non-covalently intercalated between two aromatic side chains on an oligopeptide, and an antibody or antibody fragment covalently attached to the oligopeptide for targeting to cancer cells.

U.S. Pat. No. 6,617,306 teaches a carrier for the in vivo delivery of a therapeutic agent, the carrier and therapeutic agent linked by a disulfide bond. According to U.S. Pat. No. 6,617,306, the carrier comprises a polymer, and at least one thiol compound conjugated to the polymer, such that the thiol group of the thiol compound and the thiol group of the therapeutic agent form a disulfide bond.

International Patent Application Publication No. WO 00/33888 teaches cleavable anti-tumor and anti-inflammatory compounds comprising a therapeutic agent capable of entering a target cell, an oligopeptide, a stabilizing group and an optional linker.

International Patent Application Publication No. 2005/072061 and U.S. Pat. Nos. 7,989,188 and 8,993,278 disclose compounds comprising a drug covalently linked to a functional group of an amino acid side chain, such compounds are useful for targeting drugs to neoplastic cells.

There remains an unmet need for methods of treating cancer which comprise administering to cancer patients compounds having antitumor activity but reduced cytotoxicity to normal tissues.

SUMMARY OF THE INVENTION

The present invention provides prodrugs comprising cytarabine conjugated to a single amino acid selected from the group consisting of aspartic acid, glutamic acid, asparagine, and glutamine, for use in treating neoplastic diseases in medically compromised subjects.

The present invention is based in part on the unexpected discovery that administering a compound designated herein below Astarabine®, i.e., a conjugate of cytarabine and aspartic acid wherein cytarabine is covalently attached to the carboxyl group of the side chain of aspartic acid, to elderly patients having acute lymphocytic leukemia (ALL) or acute myeloid leukemia (AML), prolonged the survival of these patients.

It is known that the maximal standard of care dose of cytarabine that can be administered to patients of 75 or more years of age who have leukemia or lymphoma is 20 mg/m$^2$ of the subject's surface area. However, most of the patients at this age cannot tolerate even this low dose of cytarabine due to its severe side effects, and therefore are not treated with cytarabine at all. It is now disclosed for the first time that the prodrug Astarabine® administered to patients of 75 or more years of age having AML or ALL was safe and well tolerated at a daily dose of about 2 g/m$^2$ or even at higher doses. The prodrug Astarabine® was effective in attenuating or even eradicating newly diagnosed leukemia as well as secondary leukemia in elderly patients.

It is further disclosed that Astarabine® can be administered to elderly patients, i.e., 60 years old or older, at doses which are significantly higher (e.g., 5-30 times higher) than the maximal standard of care dose of cytarabine, and at such doses Astarabine® did not exert significant drug-related adverse effects during or post treatment.

According to one aspect, the present invention provides a method of treating a neoplastic disease, the method comprising administering to a subject in need of such treatment a pharmaceutical composition comprising a therapeutically effective amount of a compound, or a pharmaceutically acceptable salt thereof, having the general formula (I):

A-Cytarabine    (I)

wherein A denotes an amino acid residue, the amino acid is selected from the group consisting of aspartic acid, glutamic acid, asparagine and glutamine;

wherein cytarabine is attached to A through the side chain functional group of A; and wherein the subject is a medically compromised subject who is not amenable to treatment with cytarabine.

According to one embodiment, A is aspartic acid residue and the compound is represented by the structure of formula (1), designated Astarabine®:

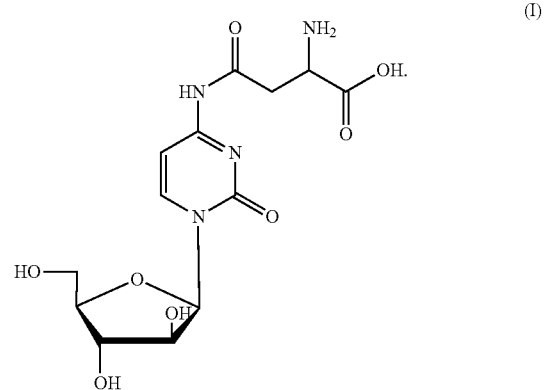

According to another embodiment, A is glutamic acid residue and the compound is represented by the structure of formula (2):

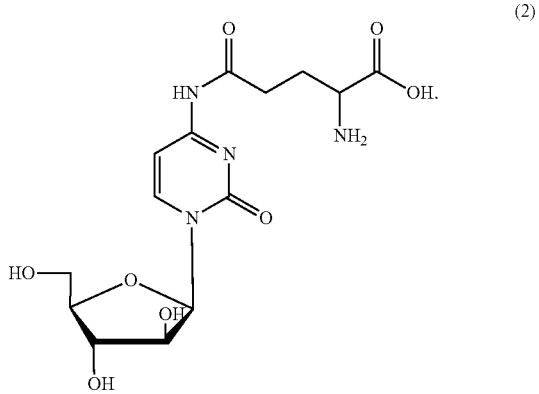

(2)

According to some embodiments, the pharmaceutically acceptable salt is a salt of an organic or inorganic acid or residue of an acid. According to additional embodiments, the acid is selected from the group consisting of acetic acid, hydrochloric acid, methanesulfonic acid, phosphoric acid, citric acid, lactic acid, succinic acid, tartaric acid, boric acid, benzoic acid, toluenesulfonic acid, benzenesulfonic acid, ascorbic acid, sulfuric acid, maleic acid, formic acid, malonic acid, nicotinic acid and oxalic acid. Each possibility represents a separate embodiment of the invention. According to one embodiment, the compound is Astarabine® and the pharmaceutically acceptable salt is acetate salt. According to another embodiment, the compound is Astarabine® and the pharmaceutically acceptable salt is hydrochloride salt.

According to additional embodiments, the neoplastic disease is selected from the group consisting of hematological cancers and non-hematological cancers. According to further embodiments, the hematological cancer is selected from the group consisting of leukemias, lymphomas, multiple myeloma, and non hematological such as Myelodysplastic Syndromes (MDS). Each possibility represents a separate embodiment of the invention.

According to yet further embodiments, the leukemia is selected from the group consisting of Acute Myeloid Leukemia (AML), Acute Lymphoblastic Leukemia (ALL), Chronic Myeloid Leukemia (CML), and Chronic Lymphoblastic Leukemia (CLL). Each possibility represents a separate embodiment of the invention.

According to still further embodiments, the AML is selected from the group consisting of newly diagnosed AML, secondary AML, and relapsed/refractory AML. Each possibility represents a separate embodiment of the invention.

According to further embodiments, the lymphoma is selected from Hodgkin's Lymphoma and Non-Hodgkin's Lymphoma (NHL).

According to some embodiments, the medically compromised subject is selected from the group consisting of elderly subjects, subjects having hepatic dysfunction, subjects having renal dysfunction, subjects having pancreatic dysfunction, subjects having bone marrow dysfunction, subjects having cerebellar dysfunction, subjects having immunologic disorder, subjects having any other organ dysfunction which limits the use of cytarabine, subjects having relapsed or refractory hematological cancers, and any combination thereof. Each possibility represents a separate embodiment of the invention.

According to additional embodiments, the elderly subject is a subject of 50 or more years of age, such as of 60, 70, 75 or more years of age. Each possibility represents a separate embodiment of the invention.

According to further embodiments, Astarabine® is administered in a daily dosage of at least 2, 3, 5, 10, 15, 20, or at least 30 times greater than the maximal standard of care dose of cytarabine alone. Each possibility represents a separate embodiment of the invention.

According to yet further embodiments, Astarabine® is administered in a daily dose ranging from about 0.3 g/m² to about 10 g/m², such as in a daily dose of about 0.3 g/m², 0.5 g/m², 0.8 g/m², 1 g/m², 1.5 g/m², 2 g/m², 2.3 g/m², 2.5 g/m², 3 g/m², 3.5 g/m², 4 m², or 4.5 g/m² of the subject's surface area or any value in-between. Each possibility represents a separate embodiment of the invention.

According to still further embodiments, the pharmaceutical composition is administered parenterally. According to further embodiments, the pharmaceutical composition is administered intravenously, intraperitoneally, intramuscularly, subcutaneously, intradermally, transdermally, or intravesicularly. Each possibility represents a separate embodiment of the invention. According to a certain embodiment, the pharmaceutical composition is administered intravenously. According to an exemplary embodiment, the pharmaceutical composition is administered by intravenous infusion for a period ranging from 15 minutes to 3 hours, such as for 30 minutes to one hour.

According to additional embodiments, the pharmaceutical composition is administered once a day for at least 3 days, such as for 3 days, 4, 5, 6, 8, 10, 12, or for 14 consecutive days or any integer in-between. According to further embodiments, the pharmaceutical composition is administered once a day for 6 consecutive days at least twice a month. According to yet further embodiments, the pharmaceutical composition is administered once every other day for at least one week, at least two weeks, three weeks or at least one month.

According to one exemplary embodiment, the compound is Astarabine® acetate, the subject is of at least 75 years of age having AML or ALL, and the pharmaceutical composition is administered at a daily dosage of at least two times greater than the maximal standard of care dose of cytarabine.

According to another exemplary embodiment, the compound is Astarabine® hydrochloride, the subject is of at least 75 years of age having AML or ALL, and the pharmaceutical composition is administered at a daily dosage of at least two times greater than the maximal standard of care dose of cytarabine.

According to another aspect, the present invention provides a method of treating a neoplastic disease, the method comprising administering to a subject in need of such treatment a pharmaceutical composition comprising a therapeutically effective amount of a compound, or a pharmaceutically acceptable salt thereof, represented by the structure of formula I:

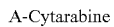

(I)

wherein A denotes the residue of an amino acid, the amino acid is selected from the group consisting of aspartic acid, glutamic acid, asparagine, and glutamine;

wherein cytarabine is attached to A through the side chain functional group of A; and wherein adverse effects of the compound are reduced compared to the adverse effects of the non-conjugated cytarabine so that the compound can be administered in a dosage of at least two times greater than the maximal standard of care dose of cytarabine, without the subject experiencing dose limiting toxicity.

According to one embodiment, A is aspartic acid residue and the compound is represented by the structure of formula (1), designated Astarabine®:

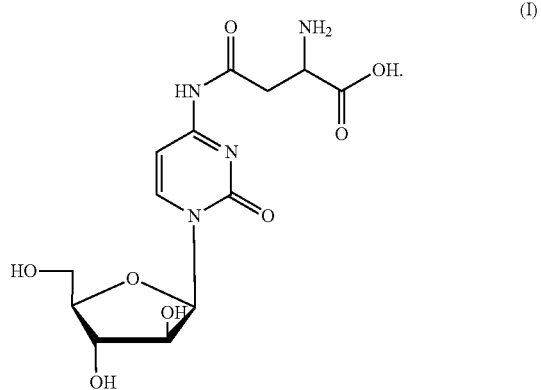

According to another embodiment, A is glutamic acid residue and the compound is represented by the structure of formula (2):

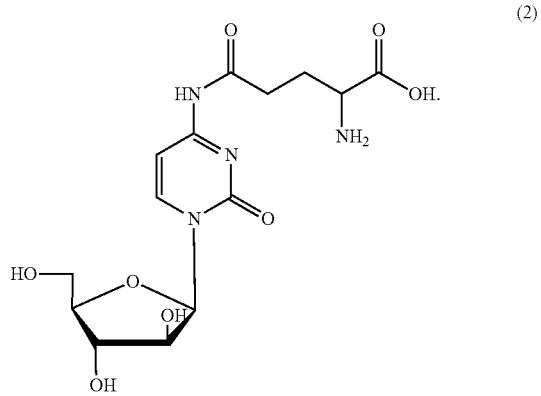

According to some embodiments, the pharmaceutically acceptable salt is a salt of an organic or inorganic acid or residue of an acid. According to additional embodiments, the acid is selected from the group consisting of acetic acid, hydrochloric acid, methanesulfonic acid, phosphoric acid, citric acid, lactic acid, succinic acid, tartaric acid, boric acid, benzoic acid, toluenesulfonic acid, benzenesulfonic acid, ascorbic acid, sulfuric acid, maleic acid, formic acid, malonic acid, nicotinic acid and oxalic acid. Each possibility represents a separate embodiment of the invention. According to a certain embodiment, the compound is Astarabine® and the pharmaceutically acceptable salt is acetate salt. According to another embodiment, the compound is Astarabine® and the pharmaceutically acceptable salt is hydrochloride salt.

According to additional embodiments, the neoplastic disease is selected from the group consisting of hematological cancers and non-hematological cancers. According to further embodiments, the hematological cancer is selected from the group consisting of leukemias, lymphomas, multiple myeloma, and non hematological such as Myelodysplastic Syndromes (MDS). Each possibility represents a separate embodiment of the invention.

According to yet further embodiments, the leukemia is selected from the group consisting of Acute Myeloid Leukemia (AML), Acute Lymphoblastic Leukemia (ALL), Chronic Myeloid Leukemia (CML), and Chronic Lymphoblastic Leukemia (CLL). Each possibility represents a separate embodiment of the invention.

According to still further embodiments, the AML is selected from the group consisting of newly diagnosed AML, secondary AML, and relapsed/refractory AML. Each possibility represents a separate embodiment of the invention.

According to further embodiments, the lymphoma is selected from Hodgkin's Lymphoma and Non-Hodgkin's Lymphoma (NHL).

According to some embodiments, the subject is a medically compromised subject who is not amenable to treatment with cytarabine. According to further embodiments, the medically compromised subject is selected from the group consisting of elderly subjects, subjects having hepatic dysfunction, subjects having renal dysfunction, subjects having pancreatic dysfunction, subjects having bone marrow dysfunction, subjects having cerebellar dysfunction, subjects having immunologic disorder, subjects having any other organ dysfunction which limits the use of cytarabine, subjects having relapsed or refractory hematological cancers, and any combination thereof. Each possibility represents a separate embodiment of the invention.

According to additional embodiments, the elderly subject is a subject of 50 or more years of age, such as of 60, 70, 75 or more years of age. Each possibility represents a separate embodiment of the invention.

According to further embodiments, Astarabine® is administered in a daily dosage of at least 2 times to at least 30 times greater than the maximal standard of care dose of cytarabine alone, such as by 3, 5, 10, 15, 20 or 30 times greater. Each possibility represents a separate embodiment of the invention.

According to yet further embodiments, Astarabine® is administered in a daily dose ranging from about 0.3 g/m² to about 10 g/m², such as a daily dose of about 0.3 g/m², 0.5 g/m², 0.8 g/m², 1 g/m², 1.5 g/m², 2 g/m², 2.3 g/m², 2.5 g/m², 3 g/m², 3.5 g/m², 4 m², or 4.5 g/m² of the subject's surface area or any integer in-between. Each possibility represents a separate embodiment of the invention.

According to still further embodiments, the pharmaceutical composition is administered parenterally. According to further embodiments, the pharmaceutical composition is administered intravenously, intraperitoneally, intramuscularly, subcutaneously, intradermally, transdermally, or intravesicularly. Each possibility represents a separate embodiment of the invention. According to a certain embodiment, the pharmaceutical composition is administered intravenously, preferably by infusion.

According to additional embodiments, the pharmaceutical composition is administered once a day for at least 3 days, such as for 3 days, 4, 5, 6, 8, 10, 12, or for 14 consecutive days or any integer in-between. According to further embodiments, the pharmaceutical composition is administered once a day for 6 consecutive days once or twice a month. According to yet further embodiments, the pharmaceutical composition is administered once every other day for at least one week, at least two weeks, three weeks or at least one month.

According to one exemplary embodiment, the compound is Astarabine® acetate and the pharmaceutical composition is administered at a daily dosage of at least two times greater than the maximal standard of care dose of cytarabine.

According to another exemplary embodiment, the compound is Astarabine® hydrochloride and the pharmaceutical composition is administered at a daily dosage of at least two times greater than the maximal standard of care dose of cytarabine.

According to a further aspect, the present invention provides a pharmaceutical composition comprising a compound, or a pharmaceutically acceptable salt thereof, represented by the structure of formula I:

wherein A denotes an amino acid residue, the amino acid is selected from the group consisting of aspartic acid, glutamic acid, asparagine and glutamine; and wherein cytarabine is attached to A through the side chain functional group of A;

for use in treating a neoplastic disease in a medically compromised subject who is not amenable to treatment with cytarabine according to the principles of the present invention.

According to a yet further aspect, the present invention provides a pharmaceutical composition comprising a compound, or a pharmaceutically acceptable salt thereof, for use in treating a neoplastic disease, the compound is represented by the structure of formula I:

wherein A denotes the residue of an amino acid, the amino acid is selected from the group consisting of aspartic acid, glutamic acid, asparagine, and glutamine;

wherein cytarabine is attached to A through the side chain functional group of A; and wherein adverse effects of the compound are reduced compared to the adverse effects of the non-conjugated cytarabine so that the compound being administered in a dosage of at least two times greater than the maximal standard of care dose of cytarabine, without the subject experiencing dose limiting toxicity.

These and other embodiments of the present invention will become apparent in conjunction with the figures, description and claims that follow.

BRIEF DESCRIPTION OF THE FIGURES

FIG. 2A shows the growth of Molt-4 transplanted leukemia cells. FIG. 2B shows the growth of CCRF-CEM transplanted leukemia cells.

DETAILED DESCRIPTION OF THE INVENTION

Figure 1A:
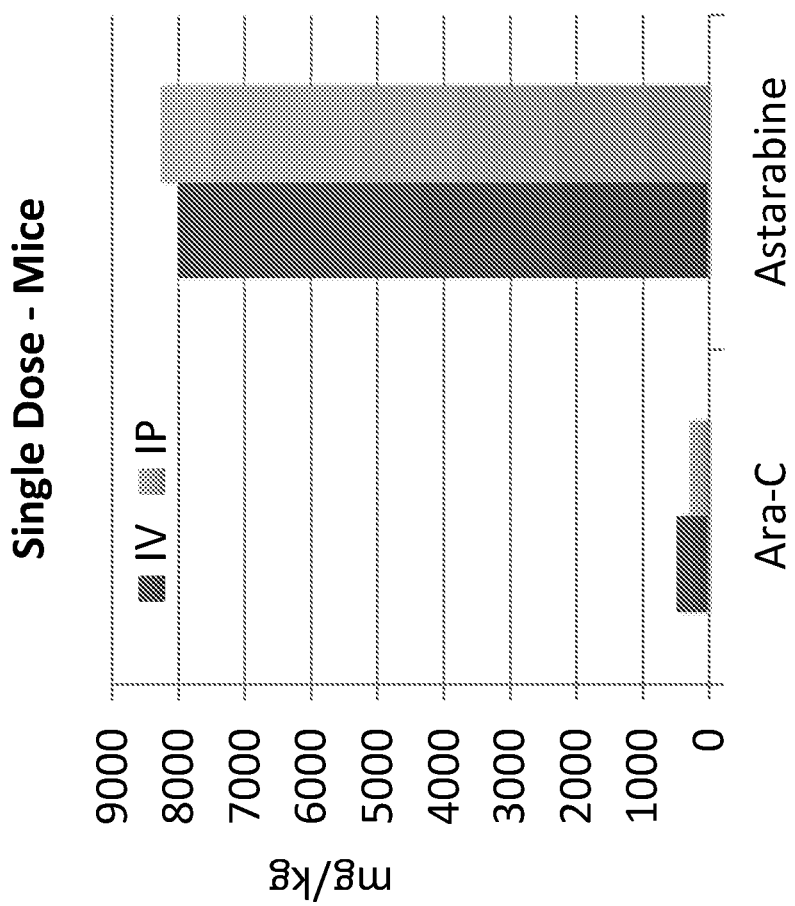
FIGS. 1A-B show in vivo measurements of maximal tolerated dose (MTD) of Astarabine®. In vivo tolerability/toxicology studies were used to determine the MTD of a single dose of Astarabine® in mice (FIG. 1A) or of 14 daily repeated doses of Astarabine® in mice (FIG. 1B). The MTD was evaluated for intravenous (IV) or intraperitoneal (IP) administration. The results are compared to MTD of cytarabine.

The present invention provides methods of treating a neoplastic disease comprising administering to medically compromised patients, particularly elderly patients of 75 or more years of age, a conjugate of cytarabine covalently linked to a single amino acid, such patients typically cannot be treated with the non-conjugated cytarabine due to its severe adverse effects, and thus are given supportive therapy only. The present invention fulfills a long-felt need for treating medically compromised patients, particularly elderly patients, who have been diagnosed as having hematological cancers, yet cannot be treated with cytarabine. The conjugates of the present invention enable treatment of these cancer patients with cytarabine at doses that would have been toxic if administered in its non-conjugated form.

Definitions

The term "medically compromised" subjects as used herein refers to a sub-population of subjects who are weakened or impaired medically so that they cannot tolerate the non-conjugated cytarabine due to its severe adverse effects. Medically compromised subjects include, but are not limited to, subjects suffering from or having renal dysfunction, hepatic dysfunction, pancreatic dysfunction, bone marrow dysfunction, cerebellar, dysfunction, immunologic disorder, any other organ, tissue or system dysfunction which limits the use of cytarabine, and a combination thereof.

The term "non-conjugated cytarabine" as used herein refers to cytarabine or an analog or derivative thereof which is free and not covalently attached to an amino acid.

The terms "renal dysfunction", "hepatic dysfunction", "pancreatic dysfunction", "bone marrow dysfunction" and "cerebellar dysfunction" refer to a state in which the organ/tissue function, e.g., kidney, liver, pancreas, bone marrow, and cerebellum, is decreased relative to a normal state. In general, organ/tissue dysfunction is a state characterized in that any one or more measurement values of inspection items for organ function are deviated from the range of normal values (reference values).

The terms "maximal standard of care dose" and "the recommended maximal dose" of cytarabine are used herein interchangeably and refer to the dosage, e.g., the daily dose, of cytarabine approved by the U.S. FDA for administration to a human subject, which dosage does not cause unacceptable adverse effects and is dependent on the subject's age and physical condition so that a subject of 50 or less years of age can be typically treated with a daily dose of cytarabine of up to 3 g/m$^2$, a subject of 50 to 60 years of age can be typically treated with a daily dose of cytarabine of up to 1.5 g/m$^2$, a subject of 60 to 75 years of age can be typically treated with a daily dose of cytarabine ranging from 0.1 g/m$^2$ to 0.5 g/m$^2$, and a subject of 75 or more years of age can be treated with a daily dose of cytarabine of up to 20 mg/m$^2$ of the subject's surface area. However, it should be noted that most of the subjects of 75 or more years of age cannot be treated with cytarabine at all due to its severe adverse effects.

The term "dose limiting toxicity" is defined in accordance with the Common Terminology Criteria of Adverse Events Version 3.0 (CTCAE). Dose limiting toxicity occurs upon administration of a compound to a subject if any of the following events are observed within a drug treatment cycle: Grade 4 neutropenia (i.e., absolute neutrophil count (ANC) ≤500 cells/mm$^3$) for 5 or more consecutive days or febrile neutropenia (i.e., fever≤38.5° C. with an ANC≤1000 cells/mm$^3$); Grade 4 thrombocytopenia (i.e., ≤25,000 cells/mm$^3$ or bleeding episode requiring platelet transfusion); Grade 4 fatigue, or a two-point decline in ECOG performance status; Grade 3 or greater nausea, diarrhea, vomiting, and/or myalgia despite the use of adequate/maximal medical intervention; Grade 3 or greater non-hematological toxicity (except fatigue); retreatment delay of more than 2 weeks due to delayed recovery from toxicity related to treatment with the compound; Grade 2 or greater cardiac toxicity of clinical significance (e.g., a decline in the resting ejection fraction to 40%-≤50% or shortening fraction to 15%-≤24%; cardiac troponin T≥0.05 ng/mL).

The term "therapeutically effective amount" of the compound is that amount of the compound which is sufficient to provide a beneficial effect to the subject to which the compound is administered. An effective amount of the compound may vary according to factors such as the disease state, age, sex, and weight of the individual.

The terms "treatment", "treat", "treating" and the like, are meant to include slowing, arresting or reversing the progression of a disease. These terms also include alleviating, ameliorating, attenuating, eliminating, or reducing one or more symptoms of a disease, even if the disease is not actually eliminated and even if progression of the disease is not itself slowed or reversed. A subject refers to a mammal, preferably a human being.

The term "residue of a drug" refers to a drug excluding the functional group that is used to attach the amino acid for the formation of the amino acid-drug conjugate A-D. Similarly, the term "residue of an amino acid" refers to an amino acid excluding the functional group that is used to attach the drug for the formation of the amino acid-drug conjugate A-D.

The term "about" in reference to a numerical value stated herein is to be understood as the stated value +/−10%.

The amino acids used in this invention are those which are available commercially or are available by routine synthetic methods. When there is no indication, either the L or the D isomer may be used.

According to one aspect, the present invention provides a method of treating a neoplastic disease, the method comprising administering to a medically compromised subject who is not amenable to treatment with cytarabine a pharmaceutical composition comprising a therapeutically effective amount of a compound, or a pharmaceutically acceptable salt thereof, having the general formula (I):

A-Cytarabine  (I)

wherein A denotes an amino acid residue, the amino acid is selected from the group consisting of aspartic acid, glutamic acid, asparagine and glutamine; and wherein cytarabine is attached to A through the side chain functional group of A.

The term "pharmaceutically acceptable salt" of a drug refers to a salt according to IUPAC conventions. Pharmaceutically acceptable salt is an inactive ingredient in a salt form combined with a drug. The term "pharmaceutically acceptable salt" as used herein refers to salts of the compounds of the general formula (I), formula (II), e.g., compounds (1) and (2), or any other salt form encompassed by the generic formulae which are substantially non-toxic to living organisms. Typical pharmaceutically acceptable salts include those salts prepared by reaction of the compounds of the present invention with a pharmaceutically acceptable mineral, base, acid or salt. Acid salts are also known as acid addition salts (see herein below). Pharmaceutically acceptable salts are known in the art (Stahl and Wermuth, 2011, Handbook of pharmaceutical salts, Second edition).

According to some embodiments of the present invention, the amino acid can have free non-modified amino and carboxyl termini, or one or both of the amino and carboxyl termini can be modified. The compound of the present invention can thus be represented by the general formula II:

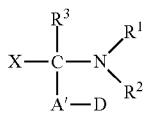  (II)

A' denotes the side chain of an amino acid, said amino acid is selected from the group consisting of aspartic acid, glutamic acid, asparagine and glutamine;

D denotes the residue of cytarabine or an analog or derivative thereof;

$R^1$, $R^2$ and $R^3$ are each independently selected from a group consisting of a hydrogen and a lower alkyl; and X is selected from the group consisting of a carboxyl, an amide and a hydrazide.

According to preferred embodiments, R1, R2 and R3 are each a hydrogen.

According to another preferred embodiment, X is a carboxylate.

According to a certain embodiment, R1, R2 and R3 are each a hydrogen and X is a carboxyl.

According to some embodiments, X is an amide group present as a carboxy amide.

Analogs of cytarabine include, but are not limited to, $N^4$-behenoyl ara-C, $N^4$-Palmitoyl-ara-C, 2'-Azido-2'-deoxy ara-C, 5'-(Cortisone 21-phosphoryl) ester of ara-C, 5'-Acyl esters of ara-C, $N^4$ Behenoyl-ara-C, ara-C conjugate with poly-$H^5$ (2-hydroxyethyl)-L-glutamine, Dihydro-5-azacytidine, 5-Aza-arabinosylcytosine and 5-Aza 2'-deoxycytidine.

According to some embodiments, the pharmaceutically acceptable salt of the compound of the invention is represented by the general formula (III):

A-D·Y  (III)

wherein A is the amino acid residue, the amino acid is selected from the group consisting of aspartic acid, glutamic acid, asparagine and glutamine;

D is cytarabine or an analog or derivative thereof, and

Y is a pharmaceutically acceptable organic or inorganic acid or residue of an acid.

According to some embodiments, Y is a pharmaceutically acceptable acid selected from the group consisting of acetic acid, hydrochloric acid, methanesulfonic acid, phosphoric acid, citric acid, lactic acid, succinic acid, tartaric acid, boric acid, benzoic acid, toluenesulfonic acid, benzenesulfonic acid, ascorbic acid, sulfuric acid, maleic acid, formic acid, malonic acid, nicotinic acid and oxalic acid. Each possibility represents a separate embodiment of the present invention.

According to exemplary embodiments, the salt form of the conjugate Astarabine® is acetate or hydrochloride.

Without wishing to be bound to any theory or mechanism of action, the amino-acid-cytarabine conjugates of the present invention are transported into the cancer cells via amino acid transporters thereby bypassing multi-drug resistance (MDR) mechanisms, and within the cells these conjugates are cleaved to release cytarabine which arrests cell growth or kill the cell. As free cytarabine and free cytarabine metabolites were detected in cancer cells, the conjugates of the present invention act as pro-drugs.

Pharmaceutical Compositions

The present invention provides pharmaceutical compositions comprising at least one of the compounds of the present invention and a pharmaceutically acceptable carrier or diluent, optionally further comprising one or more excipients.

The term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents.

For intravenous administration of a therapeutic compound, water is a preferred carrier. Saline solutions and aqueous dextrose and glycerol solutions can also be employed.

According to a certain embodiment, the formulation of Astarabine® for intravenous administration is an aqueous isotonic solution having osmolarity of about 300 mOsm and a pH of 4-8. Thus, the pharmaceutically acceptable carrier of Astarabine® can be a buffered saline solution, a buffered dextrose solution, or a buffered glycerol solution having osmolarity of about 300 mOsm and a pH of 4-8.

The buffer of Astarabine® solution can be a pharmaceutically acceptable mono-ionic buffer system or a poly-ionic buffer system having an ionization pK in the range of 4-8.

Various buffers having a pK of 4-8 can be employed for adjusting the pH of Astarabine® solution such as, for example, ACES (N-(acetamido)-2-aminoethansulfonic acid); Acetatate; N-(2-acetamido)-2-iminodiacetic acid; BES (N,N-bis[2-hydroxyethyl]-2-aminoethansulfonic acid); Bicine (2-(Bis(2-hydroxyethyl)amino)acetic acid); Bis-Tris methane (2-[Bis(2-hydroxyethyl)amino]-2-(hydroxymethyl)propane-1,3-diol); Bis-Tris propane (1,3-bis(tris(hydroxymethyl)methylamino)propane Carbonate; Citrate; 3,3-dimethyl glutarate; DIPSO (3-[N,N-bis(2-hydroxyethyl)amino]-2-hydroxypropansulfonic acid); N-ethylmorpholine; Glycerol-2-phosphate; Glycine; Glycine-amid; HEPBS (N-(2-hydroxyethyl)piperazin-N'-4-buthanesulfonic acid); HEPES (N-(2-hydroxyethyl)piperazin-N'-2-ethanesulfonic acid); HEPPS (N-(2-hydroxyethyl)piperazin-N'-(3-propanesulfonic acid)); HEPPSO (N-(2-hydroxyethyl)piperazin-N'-(2-hydroxypropanesulfonic acid); Histidine; Hydrazine; Imidazole; Maleate; 2-methylimidazole; MES (2-(N-morpholino)ethanesulfonic acid); MOBS (4-(N-morpholino)-butansulfonic acid); MOPS (3-(N-morpholino)-propanesulfonic acid; MOPSO (3-(N-morpholino)-2-hydroypropanesulfonic acid); Oxalate; Phosphate; Piperazine; PIPES (1,4-Piperazine-diethanesulfonic acid); POPSO (Piperazine-N,N'-bis(2-hydroxypropanesulfonic acid)); Succinate; Sulfite; TAPS (3-[[1,3-dihydroxy-2-(hydroxymethyl)propan-2yl]-amino]propane-1-sulfonic acid); TAPSO (3-[[1,3-dihydroxy-2-(hydroxymethyl)propan-2-yl]amino]-2-hydroxypropane-1-sulfonic acid); Tartaric acid; TES (2-[[1,3-dihydroxy-2-(hydroxymethyl)propan-2-yl]amino]ethanesulfonic acid); THAM (Tris) (2-Amino-2-hydroxymethyl-propane-1,3-diol); and Tricine (N-(2-Hydroxy-1,1-bis(hydroxymethyl)ethyl)glycine).

According to some embodiments, the buffer is a sulfonic acid derivative buffer including, but not limited to, ACES, BES, DIPSO, HEPBS, HEPES, HEPPS, HEPPSO, MES, MOBS, MOPS, MOPSO, PIPES, POPSO, Sulfite, TAPS, TAPSO, and TES buffer.

According to additional embodiments, the buffer is a carboxylic acid derivative buffer including, but not limited to, Acetatate, N-(2-acetamido)-2-iminodiacetic acid, 2-(Bis(2-hydroxyethyl)amino)acetic acid, Carbonate, Citrate, 3,3-dimethyl glutarate, Lactate, Maleate, Oxalate, Succinate, and Tartaric acid buffer.

According to further embodiments, the buffer is an amino acid derivative buffer including, but not limited to, Bicine, Glycine, Glycine-amid, Histidine, and Tricine buffer.

According to yet further embodiments, the buffer is a phosphoric acid derivative buffer including, but not limited to, Glycerol-2-phosphate and phosphate buffer.

Alternatively, the buffered saline for Astarabine® formulation can be, for example, Hank's balanced salt solution, Earle's balanced salt solution, Gey's balanced salt solution, HEPES buffered saline, phosphate buffered saline, Plasmalyte, Ringer's solution, Ringer Acetate, Ringer lactate, Saline citrate, or Tris buffered saline.

The buffered dextrose solution for Astarabine® formulation can be, for example, acid-citrate-dextrose solution or Elliott's B solution.

According to exemplary embodiments, the solutions for injection of Astarabine® is Plasma-Lyte A or Compound Sodium Lactate purchased from Baxter.

The compositions can take the form of solutions, suspensions, emulsion, tablets, pills, capsules, powders, sustained-release formulations and the like. The composition can be formulated as a suppository, with traditional binders and carriers such as triglycerides, microcrystalline cellulose, gum tragacanth or gelatin.

The pharmaceutical composition can further comprise pharmaceutical excipients including, but not limited to, sodium chloride, potassium chloride, magnesium chloride, sodium gluconate, sodium acetate, calcium chloride, sodium lactate, and the like. The composition, if desired, can also contain minor amounts of sugar alcohols, wetting or emulsifying agents, and pH adjusting agents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned.

Pharmaceutical compositions for parenteral administration can also be formulated as suspensions of the active compounds. Such suspensions may be prepared as oily injection suspensions or aqueous injection suspensions. For oily suspension injections, suitable lipophilic solvents or vehicles can be used including fatty oils such as sesame oil, or synthetic fatty acids esters such as ethyl oleate, triglycerides or liposomes. Aqueous injection suspensions may contain substances which increase the viscosity of the suspension, such as sodium carboxymethyl cellulose, sorbitol or dextran. Optionally, the suspension may also contain suitable stabilizers or agents which increase the solubility of the compounds, to allow for the preparation of highly concentrated solutions.

For transmucosal and transdermal administration, penetrants appropriate to the barrier to be permeated may be used in the formulation. Such penetrants, including for example DMSO or polyethylene glycol, are known in the art.

For oral administration, the compounds can be formulated readily by combining the active compounds with pharmaceutically acceptable carriers and excipients well known in the art. Such carriers enable the compounds of the invention to be formulated as tablets, pills, dragees, capsules, liquids, gels, syrups, slurries, suspensions, and the like, for oral ingestion by a subject. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinyl pyrrolidone, agar or alginic acid or a salt thereof such as sodium alginate.

In addition, enteric coating can be useful if it is desirable to prevent exposure of the compounds of the invention to the gastric environment.

Pharmaceutical compositions which can be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers.

In soft capsules, the active compounds may be dissolved or suspended in suitable liquids, such as fatty oils, liquid paraffin, or liquid polyethylene glycols. In addition, stabilizers may be added.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

The dosage of a composition to be administered will depend on many factors including the subject being treated, the stage of cancer, the route of administration, and the judgment of the prescribing physician.

Therapeutic Use

The present invention provides a method of treating a neoplastic disease or a viral disease comprising administering to a subject in need of such treatment a pharmaceutical composition comprising a therapeutically effective amount of a compound having the general formula (I), (II), e.g. compounds (1) or (2) or a pharmaceutically acceptable salt thereof, as described herein above, and a pharmaceutically acceptable carrier.

The neoplastic disease can be selected from hematological cancers or non-hematological cancers.

Hematological cancers include leukemias, lymphomas, myelomas, and Myelodysplastic Syndromes (MDS) including, but not limited to, myeloid leukemia, lymphocytic leukemia, e.g., acute myeloid leukemia (AML), chronic myeloid leukemia (CML), acute lymphocytic leukemia (ALL), chronic lymphocytic leukemia (CLL), Hodgkin's lymphoma, Non-Hodgkin's lymphoma, multiple myeloma, and Waldenstrom's macroglobulinemia.

The term "Myelodysplastic Syndromes" (MDS) refers to a heterogeneous group of hematopoietic malignancies characterized by blood cytopenias, ineffective hematopoiesis and a hypercellular bone marrow. The MDSs are preleukemic conditions in which transformation into acute myeloid leukemia (AML) occurs in approximately 30-40% of cases. Unless allogenic stem cell transplantation can be offered, MDS is generally considered to be an uncurable condition.

Non-hematological cancers also known as solid tumors include, but are not limited to, sarcoma, carcinoma, fibrosarcoma, myxosarcoma, liposarcoma, chondrosarcoma, osteogenic sarcoma, chordoma, angiosarcoma, endotheliosarcoma, mesothelioma, Ewing's tumor leiomydsarcoma, rhabdomyosarcoma, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma bile duct carcinoma, choriocarcinoma, seminoma, embryonal carcinoma, Wilms' tumor cervical cancer, testicular tumor, lung carcinoma, small cell lung carcinoma, bladder carcinoma, epithelial carcinoma, astrocytoma, Kaposi's sarcoma, and melanoma. Each possibility represents a separate embodiment of the invention.

Non-hematological cancers include cancers of organs, wherein the cancer of an organ includes, but is not limited to, breast cancer, bladder cancer, colon cancer, rectal cancer, endometrial cancer, kidney cancer, lung cancer, cervical cancer, pancreatic cancer, prostate cancer, testicular cancer, thyroid cancer, ovarian cancer, brain cancer including ependymoma, glioma, glioblastoma, medulloblastoma, craneopharyngioma, pinealoma, acustic neuroma, hemangioblastoma, oligodendroglioma, menangioma, neuroblastoma, retinoblastoma, and their metastasis. Each possibility represents a separate embodiment of the invention.

The present invention further provides a method for the treatment of an infection caused by a viral agent that is a cancer-causing virus. Thus, the invention provides a method for the treatment of a viral infection caused by a viral oncogene. Non-limiting examples of such viruses include human papillomavirus, Hepatitis B, Hepatitis C, Epstein-Barr virus, Human T-lymphotropic virus, Kaposi's sarcoma-associated herpesvirus, and Merkel cell polyomavirus. Each possibility represents a separate embodiment of the invention.

A viral disease can be caused by other viruses including, but not limited to, human immunodeficiency virus (HIV), herpes simplex virus (HSV), cytomegalovirus (CMV), and varicella zoster virus (VZV). Each possibility represents a separate embodiment of the invention. According to one embodiment, the viral disease is Herpes viral encephalitis.

The method of the present invention can be useful for treating a neoplastic disease in a subject having an immunological disease or disorder. Immunological diseases or disorders include, but are not limited to, rheumatoid arthritis (RA), psoriatic arthritis, systemic lupus erythematosus (SLE), lupus nephritis, Inflammatory bowel disease (IBD), irritable bowel syndrome, type I diabetes, immune thrombocytopenic purpura, multiple sclerosis, Sjorgren's syndrome, Hashimoto's thyroiditis, Grave's disease, primary biliary cirrhosis, Wegener's granulomatosis, tuberculosis, and Waldenstrom's macroglobulemia.

The method of the present invention can be useful for treating a neoplastic disease in subjects having organ dysfunction, such as hepatic dysfunction, renal dysfunction, pancreatic dysfunction, bone marrow dysfunction, and cerebellar dysfunction.

The term "hepatic dysfunction" refers to a state in which the liver function is decreased relative to a normal state. In general, hepatic dysfunction is a state characterized in that any one or more measurement values of inspection items for liver function (e.g. levels of blood AST, ALT, ALP, TTT, ZTT, total bilirubin, total protein, albumin, lactate dehydrogenase, choline esterase and the like) are deviated from the range of normal values (reference values). Hepatic dysfunction is characteristic of diseases such as, for example, fulminant hepatitis, chronic hepatitis, viral hepatitis, alcoholic hepatitis, hepatic fibrosis, liver cirrhosis, hepatic cancer, autoimmune hepatitis, drug allergic hepatopathy, and primary biliary cirrhosis.

Renal dysfunction is characteristic of diseases such as, for example, acute renal failure, glomerulonephritis, chronic renal failure, azotemia, uremia, immune renal disease, acute nephritic syndrome, rapidly progressive nephritic syndrome, nephrotic syndrome, Berger's Disease, chronic nephritic/proteinuric syndrome, tubulointerstital disease, nephrotoxic disorders, renal infarction, atheroembolic renal disease, renal cortical necrosis, malignant nephroangiosclerosis, renal vein thrombosis, renal tubular acidosis, renal glucosuria, nephrogenic diabetes insipidus, Bartter's Syndrome, Liddle's Syndrome, polycystic renal disease, interstitial nephritis, acute hemolytic uremic syndrome, medullary cystic disease, medullary sponge kidney, hereditary nephritis, and nail-patella syndrome.

Pancreatic dysfunction is characteristic of diseases such as, for example, diabetes, hyperglycemia, impaired glucose tolerance, and insulin resistance.

Bone marrow dysfunction is characteristic of diseases such as, for example, osteomyelitis, dyshematopoiesis, ion deficiency anemia, pernicious anemia, megaloblastosis, hemolytic anemia, and aplastic anemia.

Cerebellar dysfunction is characteristic of motor and neuro-behavioral disorders such as, for example, hypotonia, dysarthria, dysmetria, dysdiadochokinesia, impaired reflex, and intention tremor.

The pharmaceutical compositions of the invention may be administered by any suitable administration route selected from the group consisting of parenteral and oral administration routes. According to some embodiments, the route of administration is via parenteral administration. In various embodiments, the route of administration is intravenous, intraarterial, intramuscular, subcutaneous, intraperitoneal, intracerebral, intracerebroventricular, intrathecal or intradermal administration route. For example, the pharmaceutical compositions can be administered systemically, for example, by intravenous (i.v.) or intraperitoneal (i.p.) injection or infusion. According to a certain embodiment, the pharmaceutical composition is administered by intravenous infusion for 30 minutes to 2 hours, such as for 1 hour. The compositions of the invention may be administered locally and may further comprise an additional active agent and/or excipient.

Toxicity and therapeutic efficacy of the compounds described herein can be determined by standard pharmaceutical procedures in cell cultures or experimental animals, e. g., by determining the IC50 (the concentration which provides 50% inhibition of cell growth) and the MTD (Maximal tolerated dose in tested animals) for a subject compound. The data obtained from cell culture assays and animal studies can be used in formulating a range of dosage for use in human subjects. The exact formulation, route of administration and dosage can be chosen by the individual physician in view of the patient's condition (See e.g., Fingl, et al., 1975, in "The Pharmacological Basis of Therapeutics", Ch. 1 pp. 1).

The compound, e.g. Astarabine®, can be administered in a daily dose ranging from about 0.3 g/m$^2$ to about 10 g/m$^2$ of the subject's surface area. According to some embodiments, the compound, e.g., Astarabine®, can be administered at a daily dose ranging from about 0.5 g/m$^2$ to about 5 g/m$^2$ of the subject's surface area. According to some embodiments, the compound can be administered at a daily dose ranging from about 0.5 g/m$^2$ to about 4.5 g/m$^2$ of the subject's surface area. According to other embodiments, the compound, e.g., Astarabine®, is administered at a daily dose of about 0.3, 0.5, 0.8, 1, 1.5, 2, 2.3, 2.5, 3, 3.5, 4, 4.5, 5, 6, 7, 8, 9, 10 g/m$^2$ of the subject's surface area. Each possibility represents a separate embodiment of the invention.

According to some embodiments, Astarabine® is administered by intravenous infusion at a daily dose ranging from 0.3 g/m$^2$ to 4.5 g/m$^2$ of the subject's surface area.

According to some embodiments, the pharmaceutical composition is administered at least once a month. According to additional embodiments, the pharmaceutical composition is administered at least twice a month. According to further embodiments, the pharmaceutical composition is administered at least once a week. According to yet further embodiments, the pharmaceutical composition is administered at least twice a week. According to still further embodiments, the pharmaceutical composition is administered once a day for at least one week. According to further embodiments, the pharmaceutical composition is administered at least once a day for at least one week or until the subject is cured.

According to some embodiments, the pharmaceutical composition is administered once a day for at least 2, 3, 4, 5, 6, 8, 10, 12, or at least 14 consecutive days once a month. Alternatively, the pharmaceutical composition is administered once a day for at least 2, 3, 4, 5, 6, or 12 days twice a month, or further alternatively the pharmaceutical composition is administered every day or twice a week until the patient is cured.

In some embodiments, where the pharmaceutical composition is used for preventing recurrence of cancer, the pharmaceutical composition may be administered regularly for prolonged periods of time according to the clinician's instructions.

In some cases it may be advantageous to administer a large loading dose followed by periodic (e.g., weekly) maintenance doses over the treatment period. The compounds can also be delivered by slow-release delivery systems, pumps, and other known delivery systems for continuous infusion. Dosing regimens may be varied to provide the desired circulating levels of a particular compound based on its pharmacokinetics. Thus, doses are calculated so that the desired circulating level of a therapeutic agent is maintained.

Typically, the effective dose is determined by the activity and efficacy of the compound and the condition of the subject as well as the body weight or surface area of the subject to be treated. The dose and the dosing regimen are also determined by the existence, nature, and extent of any adverse side effects that accompany the administration of the compounds in a particular subject.

The following examples are to be considered merely as illustrative and non-limiting in nature. It will be apparent to one skilled in the art to which the present invention pertains that many modifications, permutations, and variations may be made without departing from the scope of the invention.

Example 1

Effect of Astarabine® on Different Cell Lines

The effect of Astarabine® on different cell lines was evaluated. Briefly, various cell lines were obtained from ATCC or ECACC. Hematological cells were grown in RPMI medium containing 10-20% FBS and 1% glutamine. Solid tumor cells were grown in DMEM medium containing 10-20% FBS and 1% glutamine. Cells were seeded into 96-well plates, 50,000 cells/ml, 0.2 ml per well. Test substances were diluted in saline or PBS and added in final concentrations of 0.1 nM to 10 µM, in a volume of 20 µl. The study was conducted in triplicates, PBS was used as control. Plates were incubated for 72 hr at 37° C., 5% $CO_2$. At the end of the exposure period, a MTT assay using the MTT reagent [3-(4,5-dimethylthiazol-2-yl)-2,5-diphenyltetrazolium bromide] was performed. MTT was added to each well at a concentration of 5 mg/ml in a volume of 0.02 ml. Plates were incubated at 37° C. for 3 h. The plates were centrifuged at 3500 rpm for 5 minutes and the supernatant was aspired. The pellets which contained MTT crystals were each dissolved in 0.2 ml DMSO. Absorbance was determined using ELISA reader at a wavelength of 570 nm.

The results are summarized in Table 1.

TABLE 1

| $IC_{50}$ values of Astarabine ® vs. cytarabine in tumor cell lines. | | | | | |
|---|---|---|---|---|---|
| Cell line | Cell type | Units | $IC_{50}$ Astarabine ® | $IC_{50}$ cytarabine | Cytarabine in literature |
| Molt-4 | Human acute lymphoblastic leukemia | nM | 4.0-24.0 | 1.1-12.3 | 29 ± 1.8*[1] |
| HL-60 | Human promyelocytic leukemia | nM | 255.7-276.2 | 49.6-165.2 | 37 ± 6.1*[2] |

TABLE 1-continued

IC$_{50}$ values of Astarabine ® vs. cytarabine in tumor cell lines.

| Cell line | Cell type | Units | IC$_{50}$ Astarabine ® | IC$_{50}$ cytarabine | Cytarabine in literature |
|---|---|---|---|---|---|
| CCRF-SB | Human acute lymphoblastic leukemia | µM | 11-21.4 | 1.9-3.1 | 4.2*[3] |
| K562 | Human chronic myelogenous leukemia | nM | 194.0-516.0 | 46.1-380.6 | |
| RPMI8226 | Human myeloma | µM | 33.4-144 | 9.7-63 | |
| CCRF-CEM | Human Caucasian acute lymphoblastic leukemia T lympoblastoid line | nM | 23.3-40.8 | 3.1-25.2 | 30*[3] |
| THP-1 | Human monocytic leukemia | µM | 7.1-52 | 2.3-5.5 | |
| SU DHL-1 | Human large cell lymphoma | nM | 314-335 | 124-524 | |
| Kasumi-1 | Human acute myeloblastic leukemia | µM | 7.6 | No response | |
| MEG 01 | Human chronic myelogenous leukemia | µM | 1.7 | 1.2-5.6 | |
| SU DHL-5 | Human B-cell non Hodgkin's lymphoma | nM | 196 | 323 | |
| RS 4:11 | Human acute lymphoblastic leukemia | nM | 27.1 | 26.4 | |
| P388.D1 | Mouse lymphoid macrophage | µM | 1.9-2.6 | 0.6-0.9 | |
| Ll210 | Mouse DBA/2 lymphocytic leukemia | nM | 39.4-116.4 | 12.2-16.4 | 40 ± 9*[4] |
| HepG2 | Human hepatocellular carcinoma | µM | 7-7.5 | 0.98-1.16 | 0.185 ± 0.24*[5] |
| NCIH727 | Human lung non small cell carcinoma | µM | 1.3-2.8 | 0.59-0.77 | |
| A2780 | Human ovarian carcinoma | nM | 457.4 | 72.0-113.8 | 14 ± 4*[6] |
| HT29 | Human colon adenocarcinoma | µM | No response | No response | |
| LOVO | Human colon adenocarcinoma | µM | No response | No response | |

*[1] Ogbomo et al., Neoplasia 10(12): 1402-1410, 2008;
*[2] Qin et al., Clin, Cancer Res. 13(14): 4225-4232, 2007;
*[3] Manfredini et al., Bioorg. Med. Chem. 8: 539-547, 2000;
*[4] Breistol et al., Cancer Res. 59: 2944-2949, 1999;
*[5] Grov et al., Cancer Res. 55: 3008-3011, 1995;
*[6] Ruiz Van Haperen, Cancer Res. 54: 4138-4143, 1994.

The results demonstrated that most of the hematological cancer cell lines assayed were sensitive to Astarabine®, while solid tumor cell lines were less sensitive.

Astarabine® metabolite assay in human leukemia cell lines detected free cytarabine metabolites, indicating that Astarabine® is a pro-drug of cytarabine.

Example 2

Maximal Tolerated Dose and Efficacy of Astarabine® in Mice

Maximal tolerated dose (MTD) of Astarabine® injected once or for multiple injections intrperitoneally (IP) or intravenously (IV).

Single dose IP: Ten weeks of age IRC mice were injected IP with a single dose of Astarabine®, ranging from 1428 to 8271 mg/kg (50 to 300 mg/mice, respectively). Clinical evaluation included mobility observations, food and water consumption. Mice in all groups showed normal behavior. After 7 days, the mice were sampled for hematology and biochemistry and then subjected to necropsy.

Blood samples obtained from mice injected with the high dose of Astarabine® (8271 mg/kg) showed normal results after 7 days of recovery. In all mice, all tissues were indicated as normal, with no macroscopic findings. Concentration of 8271 mg/kg Astarabine® administered by IP route was considered as MTD of Astarabine® single dose IP acute toxicity.

Repeated dose IP: Astarabine® was administered IP to IRC mice for 7 days in elevated dosages from 156 to 781 mg/kg/day (5 to 25 mg/mouse/day, respectively).

All mice were inspected daily during drug administration and recovery period. Clinical evaluation included mobility observations, food and water consumption. Mice in all groups showed normal behaviour during the administration and recovery periods. Hematology and biochemical blood tests were shown normal at the end of the experiment. Gross necropsy showed no abnormal findings.

Concentration of 781 mg/kg/day Astarabine® administrated IP for 7 days, a dose which is accumulative dose of 5467 mg/kg, was considered as the MTD (maximal tolerated dose) in mice.

Single dose IV: IRC mice were injected once IV with Astarabine® in a dose ranging from 1000 to 8000 mg/kg. The mice were evaluated for 14 days. The results indicated that Astarabine® at a dose of 8000 mg/kg was tolerated by both male and female ICR mice. The following parameters: clinical signs, body weight, food consumption and blood analysis, were normal for both male and female mice at this dose, i.e., 8000 mg/kg. There was no drug dependent death in this dose level. It is therefore concluded that 8000 mg/kg is the MTD of Astarabine® in mice for a single IV administration.

Figure 1B:
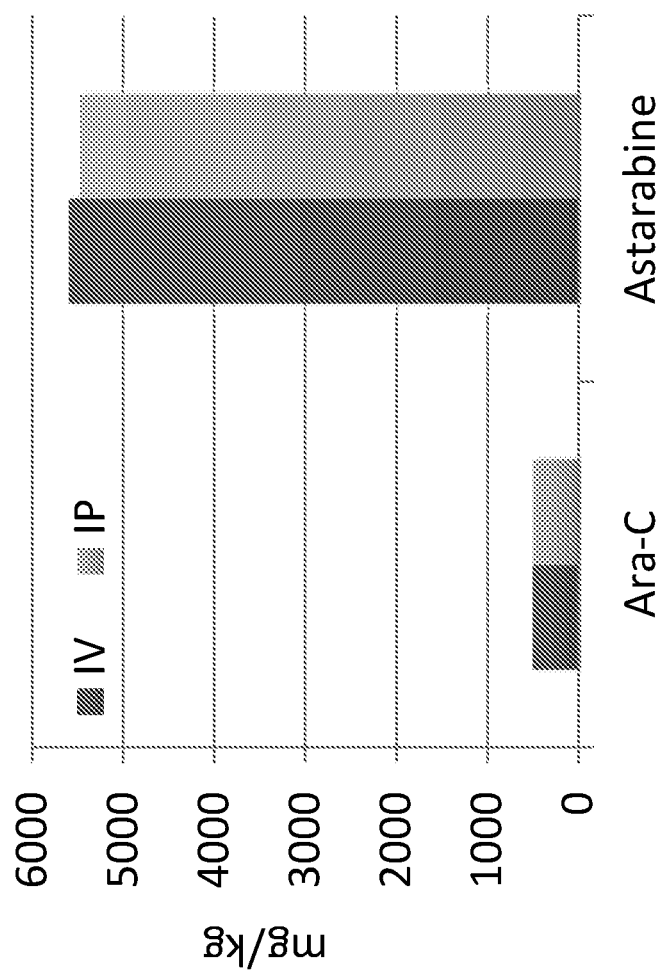

Repeated dose IV: IRC mice were injected with Astarabine® IV daily for 14 days in a dosage ranging from 400 mg/kg/day to 1200 mg/kg/day. Based on the results of this 14 days intravenous repeated dose study in mice, it was concluded that the IV maximal tolerated dose for Astarabine® is 400 mg/kg/day, administrated for 14 consecutive days. The total administered dose in this group was 5600 mg/kg. All measured parameters such as clinical observations, neurobehavioral observations, motor activity observations, body weight, food consumption, blood analysis and urine analysis, were within the normal range as compared to the non-treated group. Thus, Astarabine® in a concentration of 400 mg/kg/day was considered as the NOAEL (No Adverse Effect Level) in mice. In vivo tolerability/toxicology studies to determine the MTD of a single dose in mice are shown in FIG. 1A and of repeated doses in mice are shown in FIG. 1B.

Next, the efficacy of Astarabine® in vivo was studied on a human leukemia (Molt-4 and CCRF-CEM cells) hollow fiber model transplanted in nude mice. Astarabine® was injected at doses of 6.25 mg/mouse/day and 25 mg/mouse/day intraperitoneally (IP), daily, for 7 consecutive days; cytarabine was injected at a dose of 1.5 mg/mouse/day. Leukemia cell growth was measured using the MTT assay as described in Example 1 herein above.

Figure 2A:
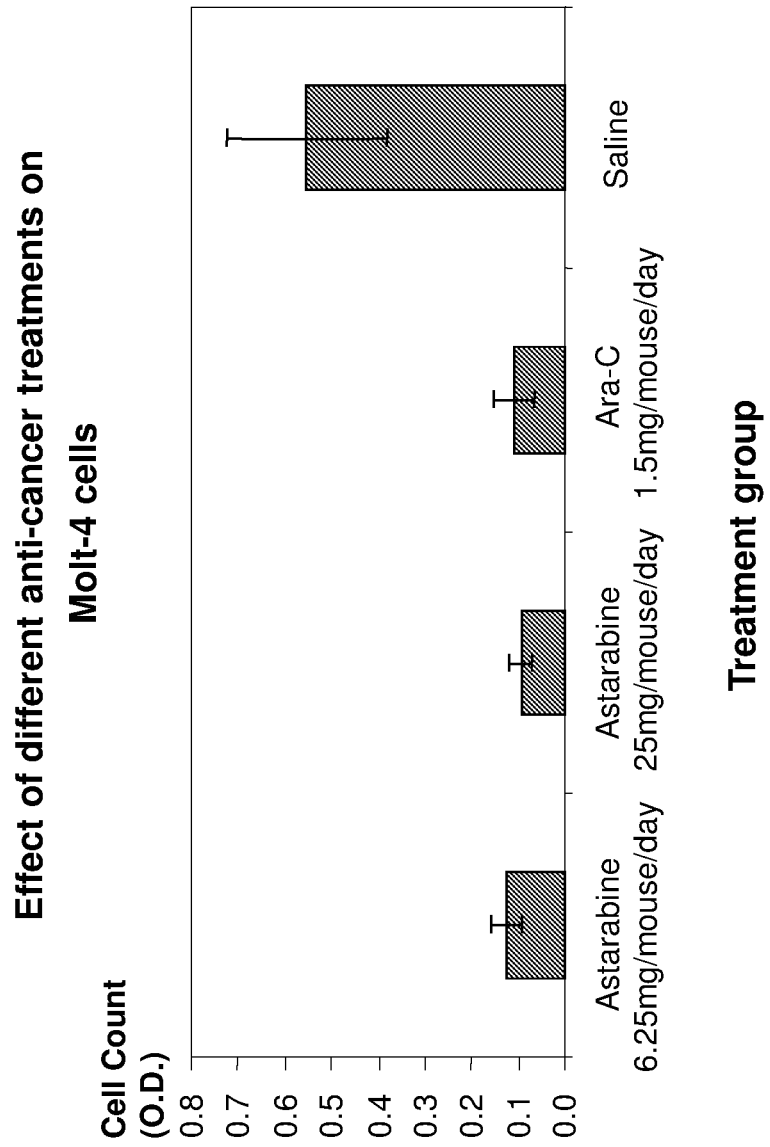
FIGS. 2A-B show the effect of Astarabine® on human leukemia growth in the hollow fiber model in transplanted nude mice in vivo. Leukemia model mice received 7 consecutive daily doses of one of the following treatments: Astarabine® in a dose of 6.25 mg/mouse/day, Astarabine® in a dose of 25 mg/mouse/day, Ara-C in a dose of 1.5 mg/mouse/day, or saline (control). In-vivo leukemia growth was measured.
Figure 2B:
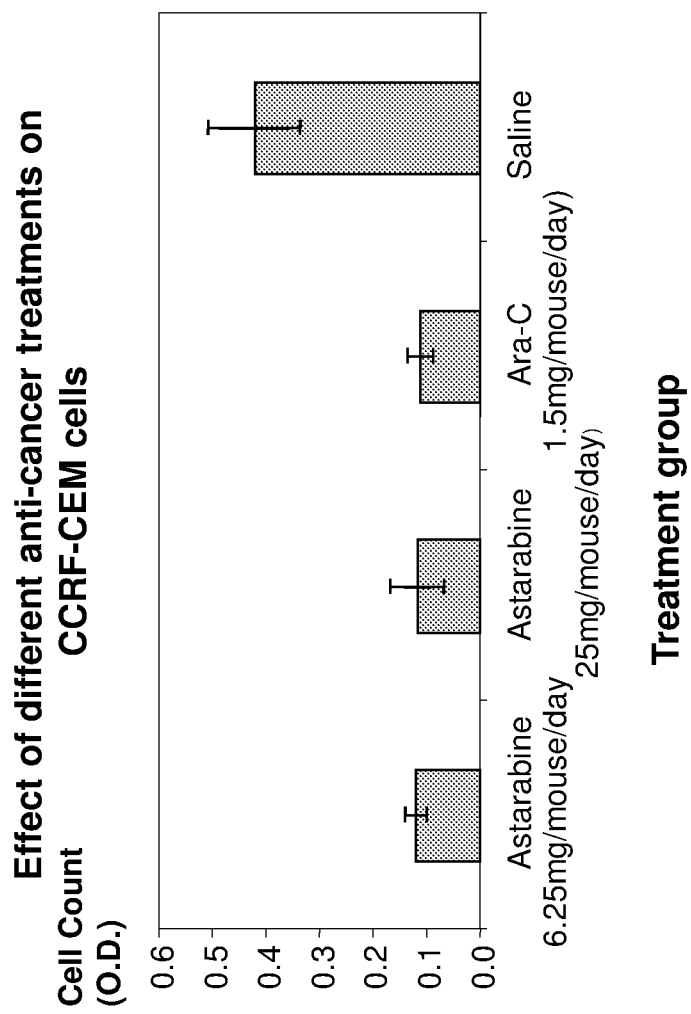

The results showed that Astarabine® at a dose of 6.25 mg/mouse/day and 25 mg/mouse/day or cytarabine at a dose of 1.5 mg/mouse/day inhibited the growth of Molt-4 cells by 76.9%, 82.8% and 81.1%, respectively, in the in-vivo hollow fiber Molt-4 leukemia model. Similarly, Astarabine® at a dose of 6.25 mg/mouse/day and 25 mg/mouse/day or cytarabine at a dose of 1.5 mg/mouse/day inhibited the growth of CCRF-CEM cells by 71.9%, 72.0% and 73.3%, respectively, in the in-vivo CCRF-CEM leukemia model. Thus, these results show a therapeutic efficacy of Astarabine® against CCRM-CEM and Molt-4 human leukemia cells. The efficacy of Astarabine® was similar to that of cytarabine. FIG. 2A shows the response in the Molt-4 leukemia model. FIG. 2B shows the response in the CCRF-CEM leukemia model.

The results indicate that Astarabine® improves drug tolerability and reduces toxicity in animals by 10-20 fold compared to the reported toxicity of cytarabine, while maintaining its anti-cancer activity. Hence, Astarabine® can serve as a safer, non-toxic alternative to cytarabine for the treatment of various leukemias.

Example 3

Astarabine Formulation and Administration

The drug Astarabine® was supplied as a sterile lyophilized powder in glass ampoules of 1 g per ampoule. The drug was dissolved in 10 ml of sterile water for injection to obtain a final concentration of Astarabine® of 100 mg/ml. Following complete dissolution in water, the drug was further diluted in an injection/infusion solution. The administered dose was calculated in g/m$^2$ according to the patient's age and medical condition.

A. Drug Dosage of 0.5 g/m$^2$:

The delivery dosage for the patient was calculated according to the following formula:

Drug dosage in g/m$^2$×Body Surface Area (BSA) of the patient in m$^2$=Dosage administered to a patient in grams (g).

Calculation example: 0.5 g/m$^2$×1.72 m$^2$=0.86 g (860 mg).

Thus, a volume of 8.6 ml (860 mg) from the 100 mg/ml Astarabine® solution were added to 500 ml of sterile buffered saline for injection, e.g., Ringer lactate, 273 mOsm/L, pH=6.5. The Astarabine® formulation was administered to the patient by infusion over 1 hour.

B. Drug Dosage of 4.5 g/m$^2$,

Calculation example: 4.5 g/m$^2$×1.65 m$^2$=7.425 g

A volume of 74.25 ml (7.425 g) from the 100 mg/ml Astarabine® solution were added to 500 ml of sterile buffered saline for injection, e.g., Plasma-lyte-A, 294 mOsm/L, pH=7.4, and were administered to the patient by infusion over 1 hour.

Example 4

Efficacy of Astarabine® in Elderly Patients

A clinical study was conducted to evaluate the performance and safety of Astarabine® in AML and ALL patients.

Study Design

Phase I/IIa, open-label, uncontrolled, single-center study enrolled patients of 18 or more years of age with relapsed or refractory acute leukemia or those unfit for intensive therapy, as judged by the treating physician. The study was approved by the Rambam IRB (approval #0384-11).

Patients were enrolled into 4 Astarabine® escalating dose cohorts, each included 3 patients. Treatment was administered as a 1-hour single daily infusion for 6 consecutive days.

Astarabine® doses for each infusion:

For age ≤50 years: 0.5 g/m$^2$, 1.5 g/m$^2$, 3 g/m$^2$, 4.5 g/m$^2$

For age >50 years: 0.3 g/m$^2$, 0.8 g/m$^2$, 1.5 g/m$^2$, 2.3 g/m$^2$

Results

The outcome of 10 patients is presented in Table 2. Nine patients had AML, of whom five patients had refractory/relapsed AML and four patients had newly diagnosed secondary AML unfit for intensive therapy. One patient had newly diagnosed ALL. Median age was 80 years.

At the end of a 10 month period:

Four patients were alive, two of whom were in continuous complete remission (CR) at 7 and 9 months post treatment.

Four patients died from disease progression, one died suddenly 7 days post treatment, an event that was postulated to be treatment unrelated. No significant adverse effects were recorded during or post therapy apart from neutropenic fever.

TABLE 2

Clinical results of treating elderly patients with Astarabine ®.

| Patient No. | Age | Astarabine Dose | Diagnosis | BM BLASTS Day 0 | Day 14 | Day 30 | Outcome | Follow-up in months |
|---|---|---|---|---|---|---|---|---|
| 1 | 75 | 0.3 gr/m²/day | Refractory AML | 100% | 90% | 83% | Died - DP | 3 |
| 2 | 81 | 0.3 gr/m²/day | Refractory AML | 100% | 64% | 70% | Died - DP | 2 |
| 3 | 27 | 0.5 gr/m²/day | Refractory AML | 90% | 37% | 60% | Died - DP | 6 |
| 4 | 76 | 0.8 gr/m²/day | Secondary AML | N/D | 39% | 63% | Died - DP | 4 |
| 5 | 81 | 0.8 gr/m²/day | Secondary AML | 80% | 5% | 0% | Alive in CR[1] | 9 |
| 6 | 63 | 0.8 gr/m²/day | Refractory AML | 85% | 100% | 100% | Died - DP | 1 |
| 7 | 90 | 1.5 gr/m²/day | ALL | 89% | 3% | 0.2% | Alive in CR | 7 |
| 8 | 86 | 1.5 gr/m²/day | Secondary AML | 63% | 80% | 8% | Alive in PR | 6 |
| 9 | 80 | 1.5 gr/m²/day | Secondary AML | 100% | N/A | N/A | Died | 1 |
| 10 | 63 | 2.3 gr/m²/day | Relapsed AML | 100% | N/A | N/A | Died | 1 |

*No significant drug-related adverse effects were observed.
PR—partial remission;
CR—complete remission;
DP—disease progression;
[1]relapsed after 9 months in CR; being considered for another Astarabine ® cycle.

The results suggest that Astarabine®, a pro-drug of cytarabine, is safe and very well tolerated, even for patients of 80 or more years of age. Remarkably, Astarabine® administration resulted in remission in three out of ten patients having acute leukemia, and this compound was particularly efficacious in patients who were newly diagnosed with leukemia.

It is appreciated by persons skilled in the art that the present invention is not limited by what has been particularly shown and described hereinabove. Rather the scope of the present invention includes both combinations and sub-combinations of various features described hereinabove as well as variations and modifications. Therefore, the invention is not to be constructed as restricted to the particularly described embodiments, and the scope and concept of the invention will be more readily understood by references to the claims, which follow.

The invention claimed is:

1. A method for treating a neoplastic disease in a subject in need thereof, the method comprising administering to the subject a compound represented by the structure:

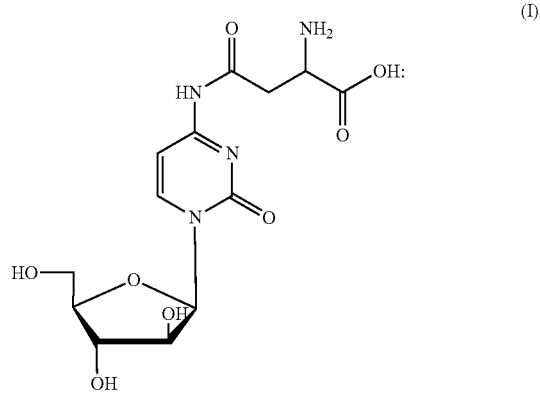

(I)

a pharmaceutically acceptable salt thereof; or a pharmaceutical composition comprising said compound or its pharmaceutically acceptable salt;
wherein the therapeutically effective amount of said compound is administered at a daily dose of from 2.5 g/m² to 10 g/m² of the subject's surface area, wherein the subject is 50 years of age or older,
and
wherein adverse effects of the compound are reduced compared to the adverse effects of standard or higher doses of the non-conjugated cytarabine.

2. The method of claim 1, wherein the compound is administered at a daily dose of at least 2.5 g/m², 3 g/m², 4.5 g/m² or 6 g/m² of the subject's surface area.

3. The method of claim 1, wherein the compound is administered at least once daily for a period of at least 3 consecutive days or via continuous infusion.

4. The method of claim 1, wherein the therapeutically effective amount of the compound is administered daily.

5. The method of claim 1, wherein the compound is administered as a pharmaceutically acceptable salt of an organic or inorganic acid selected from the group consisting of acetic acid, hydrochloric acid, methanesulfonic acid, phosphoric acid, citric acid, lactic acid, succinic acid, tartaric acid, boric acid, benzoic acid, toluenesulfonic acid, benzenesulfonic acid, ascorbic acid, sulfuric acid, maleic acid, formic acid, malonic acid, nicotinic acid and oxalic acid.

6. The method of claim 1, wherein the neoplastic disease is a hematological cancer.

7. The method of claim 6, wherein the hematological cancer is a leukemia, a lymphoma, a myeloma, or a Myelodysplastic Syndrome (MDS).

8. The method of claim 7, wherein the leukemia is acute myeloid leukemia (AML), acute lymphocytic leukemia (ALL), Chronic Myeloid Leukemia (CML), or Chronic Lymphocytic Leukemia (CLL).

9. The method of claim 8, wherein the AML is a newly diagnosed AML, a secondary AML, or relapsed/refractory AML.

10. The method of claim 1, wherein the administering is parenteral, intravenous or by intravenous infusion.

11. The method of claim 1, wherein the subject is a medically compromised subject who is not amenable to treatment with cytarabine.

12. The method of claim 11, wherein the medically compromised subject not amenable to treatment with standard-dose or high-dose cytarabine, who is an elderly subject, a subject with hepatic dysfunction, a subject with renal dysfunction, a subject with pancreatic dysfunction, a subject with bone marrow dysfunction, a subject with cerebellar dysfunction, a subject having an immunologic disorder, a subject with a relapsed or refractory hematological cancer, or any combination thereof.

13. The method of claim 5, wherein salt is hydrochloric acid.

14. The method of claim 1, wherein the neoplastic disease is a non hematological cancer.

* * * * *